(12) United States Patent
Smith et al.

(10) Patent No.: US 6,271,209 B1
(45) Date of Patent: *Aug. 7, 2001

(54) CATIONIC LIPID FORMULATION DELIVERING NUCLEIC ACID TO PERITONEAL TUMORS

(75) Inventors: Janet G. Smith; Ralph W. Niven, both of Redwood City; Yilin Zhang, San Mateo, all of CA (US)

(73) Assignee: Valentis, Inc., Burlingame, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/283,543

(22) Filed: Apr. 1, 1999

Related U.S. Application Data

(60) Provisional application No. 60/080,450, filed on Apr. 3, 1998.

(51) Int. Cl.[7] ............ A61K 31/70; A01N 43/04; C12N 15/63; C07F 9/02
(52) U.S. Cl. ............ 514/44; 435/69.1; 435/325; 435/455; 435/458; 424/450; 554/80
(58) Field of Search ............ 424/450; 435/320.1, 435/455, 458, 69.1, 325; 514/44, 76; 554/80; 536/23.1

(56) References Cited

U.S. PATENT DOCUMENTS

| | | | |
|---|---|---|---|
| 5,698,721 | * 12/1997 | Heath | 554/80 |
| 5,902,802 | * 5/1999 | Heath | 514/76 |
| 5,932,241 | * 8/1999 | Gorman | 424/450 |
| 5,958,894 | * 9/1999 | Heath et al. | 514/44 |

FOREIGN PATENT DOCUMENTS

WO96/40963 * 12/1996 (WO).

* cited by examiner

*Primary Examiner*—John L. LeGuyader
*Assistant Examiner*—Janet Epps
(74) *Attorney, Agent, or Firm*—Townsend & Townsend & Crew LLP

(57) ABSTRACT

Methods of transfecting cells in vivo, including tumor cells in the peritoneal cavity are provided. Related lipid:nucleic acid formulations adapted to transfecting cells in the peritoneal cavity are provided. Assays, including high-throughput assays for screening lipid:nucleic acids are also provided.

26 Claims, No Drawings

SEQUENCE LISTING

```
<160> NUMBER OF SEQ ID NOS: 2

<210> SEQ ID NO 1
<211> LENGTH: 17
<212> TYPE: RNA
<213> ORGANISM: Artificial Sequence
<220> FEATURE:
<223> OTHER INFORMATION: Description of Artificial Sequence:GUC hairpin
      ribozyme RNA target site
<221> NAME/KEY: modified_base
<222> LOCATION: (1)..(17)
<223> OTHER INFORMATION: n = g, u, c or a

<400> SEQUENCE: 1
```

```
nnnbcngucn nnnnnn                                              17

<210> SEQ ID NO 2
<211> LENGTH: 16
<212> TYPE: RNA
<213> ORGANISM: Artificial Sequence
<220> FEATURE:
<223> OTHER INFORMATION: Description of Artificial Sequence:GUA hairpin
      ribozyme RNA target site
<221> NAME/KEY: modified_base
<222> LOCATION: (1)..(16)
<223> OTHER INFORMATION: n = g, u, c or a

<400> SEQUENCE: 2
nnnnnguann nnnnnn                                              16
```

CATIONIC LIPID FORMULATION DELIVERING NUCLEIC ACID TO PERITONEAL TUMORS

This application claims benefit under 35 USC 119(e) of provisional application 60/080,450, filed Apr. 3, 1998.

FIELD OF THE INVENTION

The invention relates to lipid formulations particularly well-suited to the transfection of tumor cells with nucleic acids, including peritoneal tumor cells. Lipid-nucleic acid formulations, methods of transfecting cells, and assays for optimizing transfection efficiency and identifying liposomal formulation properties are provided.

BACKGROUND OF THE INVENTION

Understanding gene expression and the relationship between genes, gene expression and disease is a fundamental goal of modern medicine. Gene expression is central to many forms of disease, including inherited diseases, infectious diseases, and cancer. Procedures for studying gene expression ultimately often rely on expression of genes in vivo, as do most gene therapy approaches.

Many procedures for achieving in vivo expression of genes have relied on transfection of cells with viral vectors such as adenoviral vector mediated gene delivery, e.g., to treat cancer (see, e.g., Chen et al. (1994) *Proc. Nat'l. Acad. Sci. USA* 91: 3054–3057; Tong et al. (1996) *Gynecol. Oncol.* 61: 175–179; Clayman et al. (1995) *Cancer Res.* 5: 1–6; O'Malley et al. (1995) *Cancer Res.* 55: 1080–1085; Hwang et al. (1995) *Am. J. Respir. Cell Mol. Biol.* 13: 7–16; Haddada et al. (1995) *Curr. Top. Microbiol. Immunol.* 199 (Pt. 3): 297–306; Addison et al. (1995) *Proc. Nat'l. Acad. Sci. USA* 92: 8522–8526; Colak et al. (1995) *Brain Res.* 691: 76–82; Crystal (1995) *Science* 270: 404–410; Elshami et al. (1996) *Human Gene Ther.* 7: 141–148; Vincent et al. (1996) *J. Neurosurg.* 85: 648–654). Replication-defective retroviral vectors harboring a therapeutic polynucleotide sequence as part of the retroviral genome have also been used, particularly with regard to simple MuLV vectors. See, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)).

The transfection of cells in vivo with nucleic acids complexed with lipids, rather than viral vectors, is also becoming increasingly useful as a tool for studying gene regulation in vivo and as a delivery method for gene therapy. Lipid-DNA complexes have been used to transfect cells with a variety of nucleic acids in a variety of mammals, including mice, rats, sheep, rabbits and humans. For example, Stribling et al. (1992) *PNAS* 89:11277–11281 describe transfection of murine lung cells with various reporter constructs delivered by aerosolization of lipid-DNA complexes. See also, Debs and Zhu (1993) WO 93/24640 and U.S. Pat. No. 5,641,662. Alton et al. (1993) *Nature Genetics* 5:135–142 describe transfection of mouse lung, trachea and intestine with DNA-lipid complexes which include cationic lipids and neutral lipids. The DNA encoded the gene for human CFTR (under the control of the commonly used CMV promoter). See also, McLachlan et al. (1995) *Gene Therapy* 2:614–622.

Canonico et al. (1994) *AM. J. Respir. Cell Mol. Biol.* 10:24–29 and Canonico et al. (1994) *The Amencan Physiological Society* 415–419 describe transformation e.g., of Rabbit lung and liver by delivery of DNA-lipid complexes comprising cationic lipids. Capelen et al. (1995) *Nature Medicine* 1(1):39 describe delivery and functional replacement of CFTR activity in the nasal epithelia of human patients having cystic fibrosis using cationic lipid-cholesterol: DNA complexes. Similarly, McLachlan et al. (1996) *Gene Ther.* 3(12): 1113–23 provided similar results using DNA-cationic lipid complexes.

Applications where gene therapeutic approaches are most helpful include those in which conventional treatments are inadequate. For example, peritoneal dissemination is one of the most common complications of malignancies of the digestive system, such as gastric or pancreatic cancers. Gene therapy for peritoneal dissemination of pancreatic cancer by liposome-mediated transfer of herpes simplex virus thymidine kinase (a suicide gene) was performed in a nude mouse pancreatic cancer model. See, Aoki et al. (1997) *Human Gene Therapy* 8:1105–1113. Protection against peritoneal dissemination was observed in the model. Safety studies of the intraperitoneal injection of E1A-liposome complexes in mice have also been performed. The adenovirus 5 E1A gene has been reported to inhibit HER-2/ neu transcription and functions as a tumor suppressor gene in HER-2/ neu overexpressing cancer cells. Liposomal delivery of E1A prolongs survival of tumor-bearing mice. See, Xing et al. (1997) *Gene Therapy* 4:238–234.

A wide variety of DNA:lipid formulations have been demonstrated to be applicable to in vivo gene delivery and a very broad array of lipids have shown to have efficacy in at least one system. For example, Aoki, id. used dioctadecylamidoglycylspermine (DOGS):DNA complexes for in vivo transfection. Alton et al. (1993) *Nature Genetics* 5:135–142 used the cationic lipid (N-[1-(2,3- Dioleoyloxy) propyl]-N,N,N-trimethyl-amrnmoniummethyl-sulphate (DOTAP) for aerosol delivery of nucleic acids. Felgner, et al., (1987) *Proc. Nat. Acad. Sciences, (USA)* 84:7413–7417 describe the synthesis and use of N-[1-(2,3-dioleyloxy) propyl]-N,N,N-triethylammonium chloride (DOTMA) for transfecting cells; the composition has been used for gene delivery (sold under the trade name Lipofectin™). 1,2-dioleoyloxy-3-(trimethylammonio) propane (DOTAP) synthesis is described in Stamatatos, et al., *Biochemistry*, (1988) 27:3917–3925; this lipid has also been used for in vivo gene delivery. DOTMA, DOTAP, Dimethyl dioctadecyl ammonium bromide (DDAB), or L-lysinyl-phosphatidylethanolamine (L-PE) and a second neutral lipid, such as dioleoylphosphatidylethanolamine (DOPE) or cholesterol (Chol), have shown to be of use in in vivo cell transformation. See e.g., Debs and Zhu (1993) WO 93/24640 and U.S. Pat. No. 5,641,662. Heath (U.S. Pat. No. 5,698,721) describes cationic ampiphiles that are alkyl or alkyloxy-alkyl O-phosphate esters of diacylphosphatidyl zwitterionic compounds such as phosphatidylcholine or phosphatidylethanolamine and their use in transfecting cells with nucleic acids using the lipids as carrier molecules. Gorman WO 96/40963 describes the synthesis and use of O-ethyl-dimyristoylphosphatidylcholine (EDMPC) in conjunction with dioleoylphosphatidylethanolamine (DOPE) or cholesterol for gene delivery applications.

While lipid carriers have been shown to enhance nucleic acid delivery in vitro and in vivo, the mechanism by which they facilitate transfection is not clearly understood. While it was initially believed that lipid carriers mediated transfection by promoting fusion with plasma membranes, allowing delivery of the DNA complex into the cytoplasm, it is now generally accepted that the primary mechanism of cellular uptake is by endocytosis. While the mechanism by which cationic lipid carriers act to mediate transfection is not clearly understood, they are postulated to act in a number of ways with respect to both cellular uptake and intracellular trafficking. Some of the proposed mechanisms by which cationic lipids enhance transfection include: (i) compacting the DNA, protecting it from nuclease degradation and enhancing receptor-mediated uptake, (ii) improving association with negatively-charged cellular membranes by giving the complexes a positive charge, (iii) promoting fusion with endosomal membranes facilitating the release of complexes from endosomal compartments, and (iv) enhancing transport from the cytoplasm to the nucleus where DNA may be transcribed. When used for in vivo delivery, the role of the cationic lipid carriers is further complicated by the interactions between the lipid-nucleic acid complexes and host factors, e.g., the effects of the lipids on binding of blood proteins, clearance and/or destabilization of the complexes.

Typically, cationic lipids are mixed with a non-cationic lipid, usually a neutral lipid, and allowed to form stable liposomes, which liposomes are then mixed with the nucleic acid to be delivered. The liposomes may be large unilamellar vesicles (LUVs), multilamellar vesicles (MLVs) or small unilamellar vesicles (SUVs). The liposomes are mixed with nucleic acid in solution, at concentrations and ratios optimized for the target cells to be transfected, to form cationic lipid-nucleic acid transfection complexes. Alterations in the lipid formulation and mode of delivery allow preferential delivery of nucleic acids to particular tissues in vivo. See, PCT patent application Nos. WO 96/40962, WO 96/40963.

Thus, one problem in the art is the difficulty in identifying relevant parameters for lipid-mediated nucleic acid delivery. An additional problem is that there are so many liposomal formulations available, that it is difficult to test all possible formulations in vivo for a particular application. The present invention overcomes these problems, providing in vitro assays for selecting liposomal formulations for in vivo delivery, parameters which are important for in vivo delivery and, importantly, particularly desirable liposomal formulations for particular applications such as transfection of tumor cells in the peritoneal cavity.

SUMMARY OF THE INVENTION

It was discovered that peritoneal and intra-articular (in the joints) delivery of nucleic acids for in vivo cell transfection requires highly stable lipid-nucleic acid complexes due to the relatively high physiological amounts of salt in the peritoneal cavity. In particular, many standard lipid-nucleic acid complexes tend to precipitate at high salt, e.g., in peritoneal or intra-articular cavities in vivo. Precipitated complexes have minimal transfecting ability in vivo. Enhanced colloidial stability is, therefore, discovered to be particularly important for transfecting cancer cells in peritoneal and intra-articular cavities.

To identify nucleic acid:lipid complexes which do not precipitate under salt conditions similar to, e.g., the peritoneal cavity and which are, therefore, well suited to peritoneal gene delivery, a new in vitro stability assay was developed. In the methods of the assay, compositions for in vivo administration are selected in vitro based upon precipitation of the nucleic acid:lipid compositions in vitro. In addition to testing for precipitation, other parameters, such as resistance to a DNAse are optionally monitored, along with pH; the presence of proteins and the like can also be varied.

Using these assays, particularly good transfection agents for peritoneal delivery were identified and found to transfect tumor cells, including solid tumors, in mammalian peritoneal cavities. Accordingly, methods of transfecting tumor cells in vivo are provided. In the methods, a nucleic acid:lipid complex is administered to a mammal (e.g., a rodent (e.g., rat or mouse), primate (e.g., a macaque, chimpanzee, baboon or human), rabbit, ungulate, or the like) having a tumor. The complex includes a selected nucleic acid such as a linear DNA, a circular DNA, a DNA plasmid, a linear RNA, a circular RNA, an RNA plasmid, a ribozyme, an antisense molecule, or the like, encoding a molecule of interest (e.g., a protein, ribozyme, antisense molecule, etc.).

The complex includes a cationic lipid of the formula:

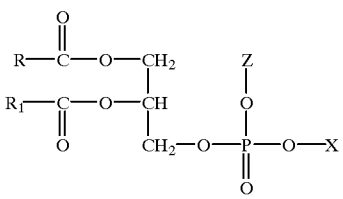

where Z is an all or alkylalkoxy, R and $R_1$ are independently selected straight chain aliphatic hydrocarbyl groups of from 11 to 29 carbon atoms, and X is a cationic moiety of the formula $-CH_2-(CH_2)_n-N^+(R_2)_3$ where n is an integer from 1 to 4 inclusive and each $R_2$ is independently hydrogen or lower alkyl. An example of such a cationic lipid is EDMPC. Typically, the complex also comprises a neutral lipid such as the preferred helper lipid 1,2diphytonoyl-sn-glycero-3-phosphoethanolamine (DiPPE), often in approximately equimolar (1:1) amounts. Common ratios for the nucleic acid:cationic lipid composition (e.g., a DNA:cationic lipid composition) is between about 1:10 and about 3:1 mg nucleic acid:μM cationic lipid, often between about 1:8 and 3:1 mg nucleic acid:μM cationic lipid. In one preferred formulation the composition is has a nucleic acid:cationic lipid ratio of about 1:8. In a second preferred embodiment, the composition has a nucleic acid:cationic lipid ratio of about 1:6. The concentration of nucleic acid (e.g., DNA) in the complex is typically in the range of about 0.1 mg/ml to 1.0 mg/ml. In one preferred formulation, the concentration of nucleic acid was about 0.25 mg/ml. The complex is typically formulated at a pH of between about 4 and about 8 inclusive, often between about 5 and 7 inclusive; in one embodiment, complexes formulated at a pH of 5 were shown to have good transfection properties.

In preferred embodiments, the nucleic acid:lipid complex does not precipitate for at least 1 hour in an aqueous solution of physiological salts at room temperature in vitro e.g., under standard agitation conditions and has a half life in peritoneal fluid which is at least 2× a naked nucleic acid. In one embodiment, the complex is. administered multiple times to increase the percentage of cells transfected, especially in tumors.

In a corresponding aspect, a preferred liposomal formulation for in vivo cell transfection in the methods as described above is provided. For example, a composition which includes a cationic lipid of the formula:

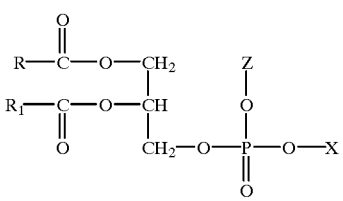

where Z is an alkyl or alkylalkoxy, R and $R_1$ are independently selected straight chain aliphatic hydrocarbyl groups of from 11 to 29 carbon atoms, and X is a cationic moiety of the formula —$CH_2$—$(CH_2)_n$—$N^+(R_2)_3$ where n is an integer from 1 to 4 inclusive and each $R_2$ is independently hydrogen or lower alkyl is provided. In one embodiment, the composition further comprises DiPPE and a selected nucleic acid, where the ratio of selected nucleic acid to cationic lipid in the composition is between about 1:10 and about 3:1 mg nucleic acid:$\mu$M cationic lipid, often between about 1:8 and 3:1 mg nucleic acid:$\mu$M cationic lipid. In one preferred formulation the composition is has a nucleic acid:cationic lipid ratio of about 1:8. In a second preferred embodiment, the composition has a nucleic acid:cationic lipid ratio of about 1:6. The concentration of nucleic acid (e.g., DNA) in the complex is typically in the range of about 0.1 mg/ml to 1.0 mg/ml. In a preferred aspect, the composition comprises physiologically acceptable excipients such as water or water/dextrose. In one embodiment, the selected nucleic acid encodes a gene such as herpes simplex virus thymidine kinase, p53, p21 or E1A, which has anti-tumor activity. The nucleic acid can also encode a variety of other genes which inhibit tumor growth, including cytokines, chemokines, viral genes, bacterial genes, tumor suppressor genes, growth factors, suicide genes, etc. The composition can also include other components, such as targeting agents which preferentially bind tumor cells, and the like.

DEFINITIONS

A "tumor cell" is a biological cell which is part of a solid tumor, or which expresses any of the known tumor marker genes, or which shows abnormal growth or differentiation.

A "nucleic acid:lipid complex" is a mixture of lipids and a nucleic acid where the lipid and the nucleic acid associate in the mixture. The term includes the use of cationic lipids, which associate with nucleic acids via ionic interactions to form nucleic acid:lipid complexes.

A "selected nucleic acid" is any RNA or DNA polymer. Commonly, the nucleic acid is a linear DNA, a circular DNA, a DNA plasmid, a linear RNA, a circular RNA, an RNA plasmid, a ribozyme, an antisense molecule, or the like, with the nucleic acid being single stranded, double stranded, in triplex formation, or a mixture of such configurations; however, synthetic polymers comprising non-naturally occurring nucleotides or non-naturally occurring linkages are also contemplated, especially as anti-sense molecules or components of ribozymes.

A "cationic lipid" is a lipid which has a net positive charge at physiological pH.

A cell is "transfected" by a nucleic acid when the nucleic acid enters the cell. The cell is stably transfected when the nucleic acid is expressed and/or replicated in the cell.

DETAILED DESCRIPTION

Several discoveries were made identifying problems which the present invention solves. First, it was discovered that transfecting cells with lipid:nucleic acid complexes was inhibited for some formulations due to precipitation of the complexes in the peritoneal cavity. Second, protection of the nucleic acid in the complex, e.g., from nucleases such as DNAse and RNAses was found to vary between different formulations.

Benchtop assays to identify preferred formulations, which protected nucleic acids from nucleases and which did not precipitate under salt and pH conditions similar to peritoneal fluid (or using peritoneal fluid), were developed. It was found that certain nucleic acid:lipid formulations were particularly well suited to in vivo intraperitoneal (i.p.) gene delivery, including for i.p. delivery to peritoneal tumor cells. Accordingly, the compositions, including new compositions, are useful for transfecting cells in vivo, particularly tumor cells in the peritoneal cavity. The compositions are also useful for intra-articular delivery (delivery to the joints).

Making Lipid-DNA Complexes

Making Selected Nucleic Acids

As described, essentially any nucleic acid can be formulated into the lipid:DNA complexes of the invention. The nucleic acid compositions of this invention, whether nuclear RNA, mRNA, cDNA, genomic DNA, plasmid DNA, or a hybrid of the various combinations, are isolated from biological sources (including recombinant sources) or synthesized in vitro. The nucleic acids of the invention are present in transformed or transfected whole cells, in transformed or transfected cell lysates, or in a partially purified or substantially pure form; when complexed to lipids, the nucleic acids are typically in substantially pure form.

Particularly preferred nucleic acids for inclusion in the complexes of the invention include those with therapeutic relevance to cancer. In particular, nucleic acids which inhibit expression of oncogenes such as HER-2/neu (e.g., the tumor suppressor E1A from adenovirus 5), or which control cell growth or differentiation are preferred components of the lipid:nucleic acid complexes of the invention. For example, nucleic acids which encode expression of cytokines, inflammatory molecules, growth factors, telomerase, growth factor receptors, oncogene products, interleukins, interferons, $\alpha$-FGF, IGF-I, IGF-II, $\beta$-FGF, PDGF, TNF, TGF-$\alpha$, TGF-$\beta$, EGF, KGF, SCF/c-Kit ligand, CD40L/CD40, VLA-4/VCAM-1, ICAM-1/LFA-1, and hyalurin/CD44; signal transfection molecules and corresponding oncogene products, e.g., Mos, Ras, Raf, and Met; and transcriptional activators and suppressors, e.g., p53, p21, Tat, steroid hormone receptors such as those for estrogen, progesterone, testosterone, aldosterone, and corticosterone or the like are known, preferred, and widely available. Nucleic acids which encode inhibitors of such molecules are also preferred, such as ribozymes and anti-sense RNAs which recognize and inhibit translation of the mRNA for any of the above. Finally, nucleic acids encoding suicide genes which induce apoptosis or other forms of cell death are preferred, particularly suicide genes which are most active in rapidly dividing cells (e.g., cancer cells), such as the herpes simplex virus thymidine kinase gene in combination with gancyclovir, the E1A gene product from adenovirus, or a variety of other viral genes. Negative selectable markers which are not activated until a counter agent is added are also appropriate. Decoy nucleic acids which encode molecules that bind to factors controlling cell growth are appropriate to some applications. Nucleic acids encoding transdominant molecules are also appropriate, depending on the application.

1. Recombinant Nucleic Acids

Commonly, the nucleic acid will be a recombinant nucleic acid such as a plasmid. General texts which describe methods of making recombinant nucleic acids include Sambrook et al., *Molecular Cloning—A Laboratory Manual* (2nd Ed.), Vol. 1–3, Cold Spring Harbor Laboratory, Cold Spring Harbor, N.Y., 1989 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 1998) ("Ausubel"); and Berger and Kimmel, *Guide to Molecular Cloning Technigues, Methods*

*in Enzymology* volume 152 Academic Press, Inc., San Diego, Calif. (Berger). In certain aspects, it is useful to make large nucleic acids which can be used to express nucleic acids of interest, or which are, themselves, nucleic acids of interest. Methods of making large recombinant RNA and DNA nucleic acids, including recombinant plasmids, recombinant lambda phage, cosmids, yeast artificial chromosomes (YACs), P1 artificial chromosomes, Bacterial Artificial Chromosomes (BACs), and the like are known. A general introduction to YACs, BACs, PACs and MACs as artificial chromosomes is described in Monaco and Larin (1994) *Trends Biotechnol* 12(7):280–286.

Product information from manufacturers of biological reagents and experimental equipment also provide information useful in known biological methods such as cloning. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., Applied Biosystems (Foster City, Calif.), Digene Diagnostics, Inc. (Beltsville, Md.) as well as many other commercial sources known to one of skill. These commercial suppliers produce extensive catalogues of compounds, products, kits, techniques and the like for performing a variety of standard methods.

2. Production of Nucleic Acids by In Vitro Amplification

In addition to cloning procedures, many in vitro amplification procedures are also used to make nucleic acids for use in the assays and lipid:nucleic acid formulations of the invention. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of in vitro amplification to amplify large nucleic acids are summarized in Cheng et al. (1994) *Nature* 369:684–685 and the references therein.

3. Synthetic Production of Selected Nucleic Acids; Ribozymes and Antisense Molecules Small selected nucleic acids (typically less than 100–150 nucleotides in length) can easily be made by chemical synthesis. Examples of selected nucleic acids which are of particular interest as components of the lipid:nucleic acid complexes of the invention include anti-sense and ribozyme molecules, which can be used to block expression of selected genes (acting, e.g., to inhibit growth of the cells, to cause apoptosis of transfected cells, or to regulate transfected cells). These nucleic acids can be made recombinantly as described above, and can be synthesized chemically, e.g., according to the solid phase phosphoramidite triester method described by Beaucage and Caruthers (1981), *Tetrahedron Letts*, 22(20):1859–1862, e.g., using an automated synthesizer, as described in Needham-VanDevanter et al. (1984) *Nucleic Acids Res.*, 12:6159–6168. Small selected nucleic acids can also be custom made and ordered from a variety of commercial sources known to persons of skill. Purification of these nucleic acids, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560. Naturally occurring nucleotides andlor synthetic nucleotides can be joined to form an oligonucleotide.

In one embodiment, the selected nucleic acid is, or encodes, an RNA molecule comprising an antisense or catalytic activity which blocks expression of a gene, e.g., in a tumor cell. By blocking expression of this selected gene, inhibition of growth is observed for the tumor.

A ribozyme is a catalytic RNA molecule that cleaves other RNA molecules (e.g., mRNA transcripts in a cell) having particular nucleic acid sequences. Common targets include RNAs comprising GUC or GUA subsequences. For example, hairpin ribozymes typically cleave one of two target sequences. GUC hairpin ribozymes cleave an RNA target sequence consisting of NNNBCN*GUCNNNNNNNN (SEQ ID NO: 1) (where N*G is the cleavage site, B is any of G, U or C, and where N is any of G, U, C, or A). GUA ribozymes typically cleave an RNA target sequence consisting of NNNNN*GUANNNNNNNN (SEQ ID NO: 2) (where N*G is the cleavage site and where N is any of G, U, C, or A). See, De Young et al. (1995) *Biochemistry* 34: 15785–15791. Ribozymes optionally comprise non-standard ribonucleotide bases, or deoxyribonucleotide bases, which can stabilize the ribozyme and make it resistant to RNase enzymes. Alternatively, the ribozyme can be modified to a phosphothio analog for use in liposome delivery systems. This modification also renders the ribozyme resistant to endonuclease activity.

General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25: 289–317 provides an overview of ribozymes in general, including group I ribozymes, hammerhead ribozymes, hairpin ribozymes, RNAse P, and axhead ribozymes. Ribozymes useful in this invention include those that cleave oncogenic cellular transcripts, ongogenic viral transcripts and the like. Methods of identifying ribozyme targets and constructing ribozymes with regions complementary to the targets are known. See, e.g., Castanotto, i.d.; De Young et al. (1995) *Biochemistry* 34: 15785–15791; and, Anderson et al. (1994) *Nucleic Acids Research* 22(6): 1096–1100.

Antisense RNA molecules have also been shown to inhibit expression of selected genes. "Sense suppression" of genes has also been observed. A number of references describe anti-sense and sense suppression, including *Antisense Strategies*, Annals of the New York Academy of Sciences, Volume 600, Eds. Baserga and Denhardt (NYAS 1992); Milligan et al., Jul. 9, 1993, J. Med. Chem. 36(14):1923–1937; *Antisense Research and Applications* (1993, CRC Press), and *Antisense Therapeutics*, ed. Sudhir Agrawal (Humana Press, Totowa, N.J., 1996).

Ribozymes or antisense molecules are optionally prepared from a DNA molecule comprising an expression cassette that, upon transcription, yields a ribozyme or antisense sequence (or both). An expression cassette can include, e.g., a promoter sequence (e.g., a polymerase II promoter, a polymerase III promoter, or the like) operably linked to a sequence encoding the ribozyme or antisense molecule. This expression cassette can also be the nucleic acid of interest which is complexed with lipid and transfected into a cell. This strategy has the advantage that amplification of the number of ribozyme or anti-sense molecules will occur upon expression in the cell, thereby amplifying the observed effect.

Making Liposomes

Lipid carriers usually contain a cationic lipid and a neutral lipid. Most in vivo transfection protocols involve forming liposomes made up of a mixture of cationic and neutral lipid and complexing the mixture with a nucleic acid. The neutral lipid is often helpful in maintaining a stable lipid bilayer in liposomes used to make the nucleic acid:lipid complexes, and can significantly affect transfection efficiency. Liposomes may have a single lipid bilayer (unilamellar) or more than one bilayer (multilamellar). They are generally categorized according to size, where those having diameters up to about 50 to 80 nm are termed "small" and those greater than about 80 to 1000 nn, or larger, are termed "large." Thus, liposomes are typically referred to as large unilamellar vesicles (LUVs), multilamellar vesicles (MLVs) or small unilamellar vesicles (SUVs).

Cationic liposomes are typically mixed with polyanionic compounds (including nucleic acids) for delivery to cells. Complexes form by charge interactions between the cationic lipid components and the negative charges of the polyanionic compounds. Polyanions of particular interest include nucleic acids, e.g., DNA, RNA or combinations of the two. Neutral lipids are optionally added to the complex.

A wide variety of liposomal formulations are known and commercially available and can be tested in the assays of the present invention for precipitation, DNA protection, pH effects and the like. Because liposomal formulations are widely available, no attempt will be made here to describe the synthesis of liposomes in general. Two references which describe a number of therapeutic formulations and methods are WO 96/40962 and WO 96/40963.

Two types of lipids are of particular interest in the present invention, because, in combination, they were determined to have good stability, to provide good protection of associated nucleic acids and to transfect tumor cells efficiently. (see also, the examples). The lipids are neutral lipids such as cholosterol, DOPE, 1,2-dilauroyl-sn-glycero-3-phosphoethanolamine (DLPE) or, more preferably, 1,2-diphytanoyl-sn-glycero-3-phosphoethanolamine (DiPPE), each as the sole neutral lipid or in combination with each other or other neutral lipids, and a cationic lipid of formula I:

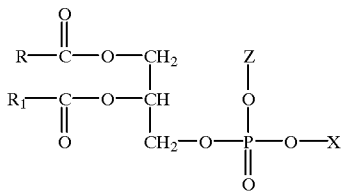

where Z is an alkyl or alkylalkoxy, R and $R_1$ are independently selected straight chain aliphatic hydrocarbyl groups of from 11 to 29 carbon atoms, and X is a cationic moiety of the formula $-CH_2-(CH_2)_n-N^+(R_2)_3$ (formula II) where n is an integer from 1 to 4 inclusive and each $R_2$ is independently hydrogen or lower alkyl. The synthesis of such cationic lipids is described in Heath, U.S. Pat. No. 5,698,721.

Preferred diacylphosphatidyl derivatives of formula I above are those in which Z is alkyl. Also preferred are those derivatives in which R and R1 independently are the alkyl or alkenyl portions of naturally occurring fatty acids containing from 14 to 24 carbon atoms inclusive (i.e., R—COOH, for example, would be the corresponding fatty acid of R—). Also preferred are those cations in which n is 1.

The cationic amphiphiles of formula I are O-substituted phosphate esters of the corresponding acidic or zwitterionic diacylphosphatidyl compounds and, in one production technique, can readily be produced from the corresponding compounds, many of which are commercially available. The acidic and zwitterionic amphiphilic compounds are illustrated by a number of known choline derivatives of the formula:

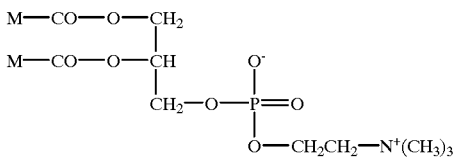

(formula III) wherein each M together with the carboxyl group to which it is attached is derived from a fatty acid moiety. The compounds of formula III are zwitterionic in character and exhibit acidic properties resulting from the presence of the phosphate group. In contrast, the O-esters of formula I are cationic, as esterification of the phosphate oxygen eliminates the negative charge on the phosphate oxygen.

In the cationic amphiphiles of formula I, each of R and R1 together with the carboxyl group to which they are attached are obtainable from straight-chain, aliphatic, hydrocarboxylic acid moieties of from 12 to 30 carbon atoms inclusive, preferably from 15 to 25 carbon atoms inclusive. Such carboxylic acid moieties are commonly referred to as fatty acid moieties because of their presence in natural fats. The acid moieties are saturated or ethylenically unsaturated, and within the cations of formula I R and R1 are the same or are different. Illustrative fatty acid moieties are lauroyl, myristoyl, palmitoyl, stearoyl, linoleoyl, tridecanoyl and oleoyl fatty acids. In an embodiment of the invention in which the cationic amphiphiles are prepared synthetically, it is advantageous for R and R1 to be the same. Alternatively, when a composition of the invention is prepared from naturally occurring materials, the R and $R_1$ moieties often will be different.

Suitable Z groups are derived from alkanols or alkoxyalkanols which are straight-chain or branched. Illustrative Z groups include methyl, ethyl, propyl, isopropyl, n-butyl, sec-butyl, pentyl, hexyl, 2-methoxyethyl, 3-ethoxypropyl, and 3-methoxypropyl. Preferred Z groups are straight-chain alkyl groups, and more preferably the Z group is methyl or ethyl, especially ethyl.

Suitable X groups, illustrative by formula because of the complexity of the nomenclature, include the following:

—CH2—CH2—N$^+$ (CH3)$_3$

—CH2—CH2—N$^+$ H$_3$

—CH2—CH2—CH2—N$^+$ (CH3)2(CH2CH3)

—CH2—CH2—N$^+$ H2(CH3)

—CH2—CH2—CH2—N$^+$ (CH3)$_3$

—CH2—CH2—N$^+$ H(CH3)$_2$

Preferred X groups are those in which n is 1 and each R2 independently is hydrogen or methyl.

The structures of cations within the scope of the invention will be apparent from the above formula I and the definitions of the terms as provided. In general, the cationic amphiphiles are O,O'-esters of a diacylphosphatidyl acid where X and Z are the esterifying groups. By analogy to the conventional nomenclature for the materials of formula III, the X group is designated in terms of the hydroxylic compound from which it is derived. Thus, in cations wherein X is cholinyl, i.e., —CH2—CH2—N$^+$ (CH3)$_3$, the cations are O-alkyl or O-alkoxyalkyl esters of a diacylphosphatidylcholine. In similar manner, an O-ester of a diacylphosphatidyl acid derivative in which X is —CH2—CH2—NH$_2$ is referred to as a O-alkyl ester of a diacylphosphatidylethanolamnine. By way of specific illustration, the cationic amphiphile of the formula

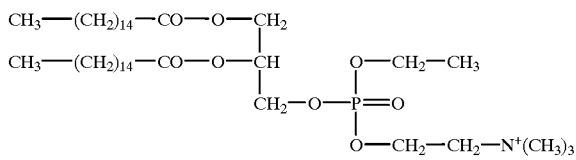

is O-ethyl dipalmitoylphosphatidylcholine. The cationic amphiphile of the formula

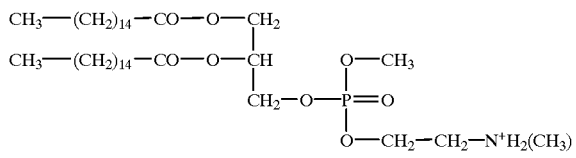

is a methyl quaternary ammonium derivative of O-methyl dipalmitoylphosphatidylethanolamine.

Cationic amphiphiles of formula I are produced by conventional synthetic processes (See also, Heath, supra). For example, a zwitterionic diacylphosphatidyl acid, e.g., a diacylphosphatidylcholine, is esterified by a substantially equimolar quantity of the hydroxylic compound from which Z is derived, e.g., methanol. In practice, esterification is facilitated by the presence of a sulfonyl halide such as methanesulfonyl chloride or p-toluenesulfonyl chloride as well as an organic base such as pyridine, picoline or lutidine. The methyl, ethyl, propyl, and butyl derivatives of dimyristoyl, dipalmitoyl, distearoyl, and egg (a mixture of acyl groups) phosphatidyl choline can all be prepared using this method.

Alternatively, a synthesis can be carried out in which the diacylphosphatidyl reactant is a compound where the X alcohol moiety is derived from an uncharged amino alcohol, e.g.,

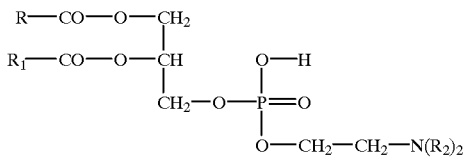

Such amine alcohol derivatives, which may be at least partially zwitterionic in character as a result of protonization during or before the actual synthesis steps, are also contacted with the desired alcohol, sulfonylhalide and base to produce the desired O-ester. However, if any R2 group is hydrogen, it is necessary to "protect" the amine function by introducing a bulky "shielding" group to prevent reaction of amino hydrogen during the esterification process. Such protection is conventional and typically comprises reaction of the amine group with triphenylmethyl chloride (trityl chloride) or t-butoxycarbonyl chloride (BOC). Subsequent to esterification, the protecting group is removed by conventional procedures such as hydrolysis. The O-ester corresponding to the compound of formula VI, if not protonated during its production, is converted to the quaternary ammonium cation of formula I by subsequent conventional protonation or reaction with an alkyl halide such as methyl bromide.

Among the naturally occurring lipids which can be employed for preparation of the cationic amphiphiles are phosphatidyl compounds, such as phosphatidyl choline (PC) and phosphatidyl ethanolamine (PE), and sphingolipids such as sphingomyelin.

A preferred cationic lipid is EDMPC which is commercially available, e.g., from Avanti Polar Lipids (Alabaster, Ala.).

The preferred neutral lipids DOPE, DLPE and DIPPE are commercially available, e.g., from Avanti Polar Lipids (Alabaster, Ala.). Cholesterol is available from, e.g., SIGMA (St. Louis Mo.).

Neutral lipids may also be synthesized by methods known in the art. Several methods are described, e.g., in Eibl, (1980) "Synthesis of Glycerophospholipids," *Chemistry and Physics of Lipids* 26:405–429. See also the references cited therein. For instance, DLPE may be synthesized starting from 1,2-dilauroylglycerol. Phosphorylation may be achieved by subsequent reactions with phosphorous oxychloride and t-butyloxycarbonylaminoethanol. The condensation product is then dissolved in formic acid to remove the protecting group. Alternatively, 1,2-dilauroyl-sn-glycerol may be converted to 1,2-dilauroyl-sn-glycero-3-phosphoric acid dichloride by phosphorylation with phosphorus oxychloride in the presence of triethylamine, in molar ratios of diacylglycerol:phosphorus oxychloride:base, 1:1.5:1.5. The excess phosphorous oxychloride is removed by evaporation and the 1,2-dilauroyl-sn-glycero-3-phosphoric acid dichloride thus obtained is reacted with ethanolamine in the presence of triethylamine (molar ratios 1:1:2). The reaction is completed after 30 min and the intermediate 1,3,2-oxazaphospholane is recrystallized from hexane. Hydrolysis of the phospholane in 2-propanol in the presence of weak acids, e.g., formic or boric acids, results in the precipitation of the phosphatidylethanolamine.

Combining Liposomes and Nucleic Acids

The lipid carriers of the invention will generally be a mixture of cationic lipid and neutral helper lipid in a molar ratio of from about 3:1 to 1:3, preferably about 1:1. The lipid carriers may include one or more cationic lipid of formula I, and may include, e.g., cholesterol, DOPE, DLPE or DiPPE alone or in combination as the helper lipid, or may include additional non-cationic helper lipids, which may be either anionic or neutral lipids. Usually, the lipid carriers will have, as the lipid components, a single cationic lipid and a single neutral lipid, preferably in approximately equimolar amounts. Lipid mixtures typically are prepared in chloroform, dried, and rehydrated in, e.g., 5% dextrose in water or a physiologic buffer to form liposomes. Low ionic strength solutions are preferred. Liposomes may be LUVs, MLVs, or SUVs. Usually, the liposomes formed upon rehydration are predominantly MLVs, and SUVs are formed from them by sonication or by extrusion through membranes with pore sizes ranging from 50 to 600 nm to reduce their size. Most preferably, the liposomes are extruded through a series of membranes with decreasing pore sizes, e.g., 400 nm, 200 nm and 50 nm.

The resulting liposomes are mixed with a nucleic acid solution with constant agitation to form the cationic lipid-nucleic acid transfection complexes. The preferred size will vary depending on use. While the primary use for the complexes of the invention are for i.p. delivery, it will be appreciated that the new compositions of the invention are also generally useful as transfection agents, including for intravenous, intra-articular and aerosolized gene delivery. Smaller transfection complexes are preferred for aerosol administration, thereby reducing shear caused by the aerosolization process. Preferred mean transfection complex size for aerosol administration is less than 5000 nm, most preferably from 50 to 300 nm. Preferred mean transfection complex size for intravenous administration is from 50 to 5000 nm, most preferably from 100 to 600 nm. Preferred mean transfection complex size for i.p. administration is from 50 to 5000 nm, most preferably from 100 to 600 nm. For tumoral delivery, direct injection or other direct administration methods are performed, or indirect (e.g., catheter-mediated) methods are performed.

Cationic lipid-nucleic acid transfection complexes can be prepared in various formulations depending on the target cells to be transfected. While a range of lipid-nucleic acid complex formulations will be effective in cell transfection, optimum conditions are determined empirically in the desired system. Lipid carrier compositions are evaluated, e.g., by their ability to deliver a reporter gene (e.g. CAT, which encodes chloramphenicol acetyltransferase, or luciferase, or β-galactosidase) in vitro, or in vivo to a given tissue or tumor type in an animal, such as a mouse, or in the assays below, which test stability, protection of nucleic acids, and the like.

For in vitro transfections, the various combinations are tested for their ability to transfect target cells using standard molecular biology techniques to determine DNA uptake, RNA and/or protein production. Typically, in vitro cell transfection involves mixing nucleic acid and lipid in cell culture media and allowing the lipid-nucleic acid transfection complexes to form for about 10 to 15 minutes at room temperature. The transfection complexes are added to the cells and incubated at 37° C. for about four hours. The complex-containing media is removed and replaced with fresh media, and the cells incubated for an additional 24 to 48 hours.

The lipid mixtures are complexed with nucleic acids in different ratios depending on the target cell type, generally ranging from about 6:1 to 1:20 μg nucleic acid:nmole cationic lipid. For transfection of airway epithelial cells, e.g., via aerosol, intratracheal, or intranasal administration, net negatively charged complexes are preferred. Preferred DNA:cationic lipid ratios for i.p. delivery are from about 1:3 to 1:20 μg DNA:nmole cationic lipid, preferably about 1:3 to 1:15, generally, about 1:3 to 1:10, and, in one embodiment, 1:8 μg DNA:nmole cationic lipid.

Additional parameters such as nucleic acid concentration, buffer type, concentration, etc., will have an effect on transfection efficiency, and can be optimized using the techniques herein. Preferred conditions are described in the examples that follow, particularly for i.p. delivery. For example, for intraperitoneal delivery, particularly to peritoneal tumors, a preferred formulation consists of EDMPC and DiPPE in a 1:1 molar ratio, 1:8 DNA: cationic lipid ratio (μg DNA: nmole cationic lipid), 0.25 mg/ml DNA, in a 2.5 mM histidine buffer, pH 5.0 and 5% w/v dextrose.

Non-lipid material, (such as biological molecules being delivered to an animal or plant cell or target-specific moieties) can be conjugated to the lipid carriers through a linking group to one or more hydrophobic groups, e.g., using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains which will allow their association with the lipid mixture without covalent linking to one or more lipid groups. For the most part, the active compounds to be bound to the lipid mixture are ligands or receptors capable of binding to a biological molecule of interest. For example, a ligand binding specifically to a receptor on a particular target cell type can be used to target delivery of the lipid carrier (with, e.g., the nucleic acid of interest) to the desired target cells. Alternatively, the active compound can be a peptide or other small molecule designed to regulate intracellular trafficking of the delivered substance, e.g., triggering endosomal release or transport into the nucleus using a nuclear localizing sequence. The active compounds bound to the lipid mixture can vary widely, from small haptens (molecular weights of about 125 to 2000) to antigens (molecular weights ranging from around 6000 to 1 million). Of particular interest are proteinaceous ligands that bind to and are internalized by specific complementary binding partners on cell surfaces. Illustrative active compounds include cytokines, interferons, hormones, antibodies to cell surface receptors or other molecules, and fragments of such compounds that retain the ability to bind to the same cell surface binding partners that bind the original (non-fragment) molecules. Of particular interest are ligands which selectively bind to cancer cells, such as IL-13.

The number of active compounds bound to a lipid carrier will vary with the size of the complex, packaging constraints, the size of the compound, the binding affinity of the molecule to the target cell receptor or ligand, and the like. Usually, the bound active molecules will be present in the lipid mixture in from about 0.001 to 10 mole percent, more usually from about 0.01 to 5 mole percent based on the percent of bound molecules to the total number of molecules available in the mixture for binding. The lipid carrier compositions are particularly useful as carriers for use in vivo, particularly in vivo in humans. Particularly where repeat administration is necessary or desirable, the carriers should be screened for toxicity. Choice of neutral lipid can modulate toxicities observed with cationic lipids in different formulations, and thus each combination should be tested separately. An animal, such as a mouse or a rabbit, can be administered one or more doses of material containing between 10 nmole and 10 μmole of the lipid to be tested, typically complexed with the intended active component (such as DNA). At various times after administration the animals are monitored for evidence of toxicity, e.g. lethargy or inflammation. The animals are sacrificed and the liver examined for toxicity. Total lipid may also be analyzed for the particular lipids or partial degradation products using, e.g., HPLC. Delivery can be by any means known to persons of skill in the art, e.g., intravenous, intraperitoneal, intratracheal, intranasal, intramuscular, intradermal, intratumoral intra-articular etc., although the present application is particularly relevant to peritoneal, intratumoral and intra-articular delivery methods.

Benchtop Assays for Identifying Optimal Formulations

To identify lipid-nucleic acid complexes which do not precipitate under physiological salt conditions such as that of the peritoneal cavity, and which are, therefore, well-suited to peritoneal gene delivery, a new in vitro assay was developed. In the methods of the assay, compositions for in vivo administration are selected in vitro based upon precipitation of the nucleic acid:lipid compositions in vitro. In the methods, a first composition which includes a first nucleic acid:lipid complex is added to a first aqueous physiological salt solution in vitro (e.g., which mimics the salt concentration in the peritoneal cavity, or which is peritoneal fluid isolated from a mammal) to provide a first nucleic acid:lipid solution. The first nucleic acid:lipid solution is incubated and monitored for precipitation of the solution in vitro (this can be observed by measuring turbidity, flow through given pore sizes, visual inspection or the like). Typically, the assay is run serially or in parallel with one to several additional nucleic acid:lipid complexes (which may have different lipids, different nucleic acids, different concentrations of nucleic acids or different ratios of lipids and nucleic acids) and the results of the precipitation of the different complexes is compared to determine which composition is the most stable in that environment. Compounds identified as being particularly stable are further tested for stability and transfecting ability in vivo.

In addition to testing for precipitation, other parameters, such as resistance to a DNAse, the effects of varying pH, effects of adding proteins (e.g., albumin) and the like can also be determined. Methods of varying pH, salt concentration, addition of proteins and the like are basic to laboratory science and known to one of skill. A variety of DNAses are commercially available, e.g., from SIGMA, St Louis, Mo.

One assay factor which effects benchtop stability is agitation (stirring or shaking accelerates precipitation). Accordingly, the assays are preferably standardized with regards to agitation. Standard agitation practices include moderate stirring or shaking.

High-throughput Screening Formats

The assays of the invention can be practiced using kits or integrated systems to increase throughput of the assay format. Most commonly, high throughput formats of the assay will utilize commercially available 96, 384 or 1536 well microtiter plates. Separate lipid:nucleic acid formulations are tested in one or more wells of the microtiter plate for their stability in varying salt solutions, varying pH, stability of DNA after addition of DNAse and the like. Assays using 96 well plates were performed.

Integrated systems for practicing the assays can include a robotic armature which transfers fluid from a source to a destination, a controller which controls the robotic armature, a precipitation detector, a data storage unit which records precipitation detection, a DNA integrity detector and an assay component such as a microtiter dish comprising assay reagents (DNA:lipid complexes, DNAse, salts, buffers and the like).

A number of well-known robotic systems are available for solution phase chemistries such as those of the present assay. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a researcher. Any of the above devices are suitable for use with the present invention. The nature and implementation of modifications to these devices (if any) so that they can operate as discussed herein are routine.

The invention also provides kits for practicing the methods noted above. The kits can include any of the compositions noted herein, and optionally further include additional components such as instructions to practice a high throughput method of screening for precipitation, one or more containers or compartments (e.g., to hold nucleic acids, lipids, cells, or the like), a control precipitation component (e.g., a lipid:DNA complex with a known precipitation time); a robotic armature for mixing fluidic kit components or the like.

High throughput fluidic devices applicable to the assays of the invention are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for performing fluidic manipulations.

Optical images viewed (and, optionally, recorded) by a camera or other recording device (e.g., a photodiode and data storage device), e.g., a turbidity measurement, are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or pentium chip- compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Where simple turbidity measurements are made, it is possible to simply monitor light absorbance of a sample at, e.g., 465 nm.

EXAMPLES

The following examples are provided by way of illustration only and not by way of limitation. Those of skill will

Example 1

Formulation Stability in Physiological Media

Studies of the physical state and distribution of 3:1 and 1:6 (mg DNA:μM lipid ratio) complexes following intraperitoneal (i.p.) administration to mice indicated that precipitation of concentrated lipid complexes and protection of the DNA were key transfection parameters. To address these issues, a series of stability experiments were designed to assess the extent of aggregation taking place in physiological salt, or salts plus albumin. In parallel, complexes at various ratios of DNA to lipid were assessed by a DNAse I protection assay with respect to their ability to protect the DNA from attack. These studies, and their results, are described in this example.

Materials and Methods

1. Lipid, DNA and Complexes.

In all cases, cationic lipid-DNA complexes were formulated with the Hamilton diluter, using standard practice. Plasmid DNA was formulated with three different liposomes. The liposomes used were EDMPC/cholesterol, EDMPC/DOPE and EDMPC/DiPPE.

2. Salt Stability Studies.

Complexes formulated at 1:6 (defined above) were added to the physiological salt solution (1:5 v/v) or physiological salt solution containing albumin (4.8 g/dL) at a constant rate using a micropipette. They were then incubated at 37° C. and checked visually for precipitation, continuously for the first fifteen minutes and every ten minutes thereafter. The particle size was obtained for complexes that had not precipitated after 8 hours and 3 days using the BrookHaven Particle Sizer.

3. DNA Protection Plasmid DNA.

Plasmid DNA was formulated with EDMPC/Cholesterol liposomes to a final concentration of 0.3125 mg/ml at 1:6 ratio (defined above) and also at 1:1 and 3:1 ratios. The samples were maintained at 37° C., and DNase I and $MgCl_2$ were added to final concentrations of 1 u/μg DNA and 1 mM respectively. Aliquots containing 30 μg of DNA (60 μl volume) were removed at 0, 1, 5, 15, 30 and 60 minutes. At each time point, the DNA was extracted using ethanol precipitation and analyzed by agarose gel electrophoresis.

Results

1. Lipid-DNA Ratio.

All of the EDMPC/Cholesterol complexes tested at a 1:6 ratio precipitated in physiological salt solution (Table 1). These complexes were stable for a longer period of time in the physiological salt solution containing albumin.

TABLE 1

Precipitation time for various complexes (min)

| DNA concentration | 1:6 ratio pH | | | 1:1 ratio pH | | | 3:1 ratio pH | | |
|---|---|---|---|---|---|---|---|---|---|
| (mg/ml) | 5 | 6 | 7 | 5 | 6 | 7 | 5 | 6 | 7 |
| BODAI/chol | | | | | | | | | |
| 0.3125 | 90'00 | 3'28 | 2'28 | — | — | — | 180' | 120' | 120' |
| 0.5 | 11'54 | 2'18 | 2'00 | — | — | — | — | — | — |
| 1.0 | 1'32 | * | 0'45 | — | — | — | — | — | — |

TABLE 1-continued

Precipitation time for various complexes (min)

| DNA concentration | 1:6 ratio pH | | | 1:1 ratio pH | | | 3:1 ratio pH | | |
|---|---|---|---|---|---|---|---|---|---|
| (mg/ml) | 5 | 6 | 7 | 5 | 6 | 7 | 5 | 6 | 7 |
| EDMPC/chol | | | | | | | | | |
| 0.3125 | 12'20 | 6'30 | 6'00 | — | — | — | — | — | — |
| 0.5 | ** | ** | ** | — | — | — | — | — | — |
| 1.0 | ** | ** | ** | — | — | — | — | — | — |

* Precipitated during preparation.
** Not made.
— No precipitation was measured at the final time point of 8 hours 2. Liposomes.

Complexes made with EDMPC/Cholesterol precipitated both in physiological salt and in salt solution containing albumin. Complexes made with other helper lipids (DOPE and DIPPE) were stable for at least three days.

3. pH Effects

BODAI complexes formed at 1:6 ratio and a final concentration of 0.3125 mg/ml demonstrated reduced stability in physiological salt as the pH was increased from 5, to 6, to 7 (Table 1). This result was most pronounced in the BODAI/cholesterol containing complex formed at 0.3125 mg/ml. As the pH increased, the stability time dropped from 20 min (pH 5), to 18 (pH 6) then 10 (pH 7).

4. DNA Protection.

This study showed a similar trend. Protection of DNA was most efficient with the 1:6 complex, followed by the 1:1 and finally the 3:1 complex. The pH also had an effect on protection of the DNA. The DNA was well protected in complexes made at pH 5 compared to complexes at pH 6 and 7.

Colloidal theory suggests that a dilute, homogeneous suspension is likely to be more stable than a concentrated, heterogeneous sample. Aggregation in a colloidal suspension is dependent on a number of factors, including charge and pH. These factors influence the size/depth of the double layer surrounding each particle. As the double layer is reduced, the attractive Van der Waals forces are able to overcome the weak repulsive forces between particles. In these experiments, a reduced pH correlated with extended stability in physiological salts. The ratio of lipid to DNA in the formulation had a direct correlation with DNA protection as the DNA was protected for a longer time in complexes with greater amounts of lipid.

In summary, EDMPC/Cholesterol complexes formulated at pH 5 are more stable in physiological salts than those at pH 6 or 7. Complexes formulated at reduced DNA concentrations (0.3125 mg/ml) are more stable in physiological salt than those formulated at high DNA concentrations (0.5 or 1.0 mg/ml). The inclusion of albumin in the physiological salt medium increased complex stability. 1:6 complexes made with EDMPC/DOPE and EDMPC/DIPPE liposomes are more stable in the physiological solutions. A higher lipid to DNA ratio provides better protection of DNA from degradation. Complexes formulated at pH 5 were most stable against DNaseI.

Example 2

Additional Formulation Stability in Physiological Media—BODAI/Cholesterol

Additional studies were performed using BODAI/cholesterol lipid:DNA complexes.

Materials and Methods
1. Lipid, DNA and Complexes.

In all cases, cationic lipid-DNA complexes were formulated with the Hamilton diluter, using standard practice.

2. Salt Stability Studies

Complexes formulated at 1:6, 1:1 or 3:1 ratios (defined above) were added to the physiological salt solution (1:5 v/v) at a constant rate using a micropipette. They were then incubated at 37° C. and checked visually for precipitation continuously for the first fifteen minutes and every ten minutes thereafter. The particle size was obtained for complexes that had not precipitated after 8 hours using the BrookHaven Particle Sizer.

3. DNA Protection

Plasmid DNA was formulated with BODAI/cholesterol liposomes to a final concentration of 0.3125 mg/ml, at 1:5, 1:1 or 5:1 ratios (defined above). The samples were maintained at 37° C., and DNase I and $MgCl_2$ added to final concentrations of 1 u/μg DNA and 1 mM respectively. Aliquots containing, 30 μg DNA (60 μl volume were removed at 0, 1, 5, 15 and 30 minutes. At each time point the DNA was extracted using ethanol precipitation and analyzed by agarose gel electrophoresis.

Results

1. Lipid.-DNA Ratio.

All of the complexes tested at a 1:6 ratio precipitated in physiological salt (Table 2).

TABLE 2

| Liposomes | pH | DNA conc. | ratio | init. size | ppt time/8 hrs size | size on day 3 |
|---|---|---|---|---|---|---|
| Salts | | | | | | |
| EC | 5 | 0.3125 | 1:06 | 206 | 20 mins | ppt |
|  | 6 | 0.3125 | 1:06 | 204.5 | 18 mins | ppt |
|  | 7 | 0.3125 | 1:06 | 208.4 | 10 mins | ppt |
| E/DOPE | 5 | 0.3125 | 1:06 | 202.6 | 219 | 243.6 |
|  | 6 | 0.3125 | 1:06 | 204.5 | 212 | 664.7 |
|  | 7 | 0.3125 | 1:06 | 206.4 | 221 | 703.2 |
| E/DiPhy | 5 | 0.3125 | 1:06 | 208.6 | 212 | 318.7 |
|  | 6 | 0.3125 | 1:06 | 207.6 | 218 | 345.8 |
|  | 7 | 0.3125 | 1:06 | 205.5 | 219 | 378.9 |
| Salts + Albumin | | | | | | |
| EC | 5 | 0.3125 | 1:06 | 206 | 120 mins | ppt |
|  | 6 | 0.3125 | 1:06 | 204.5 | 60 mins | ppt |
|  | 7 | 0.3125 | 1:06 | 208.4 | 30 mins | ppt |
| E/DOPE | 5 | 0.3125 | 1:06 | 202.6 | 210 | 215.1 |
|  | 6 | 0.3125 | 1:06 | 204.5 | 210 | 456.2 |
|  | 7 | 0.3125 | 1:06 | 206.4 | 210.8 | 502.1 |
| D/DiPhy | 5 | 0.3125 | 1:06 | 208.6 | 211 | 305 |
|  | 6 | 0.3125 | 1:06 | 207.6 | 212 | 297.6 |
|  | 7 | 0.3125 | 1:06 | 205.5 | 210 | 287.4 |

Precipitation was Reduced in the Presence of Albumin.

The effects of pH and DNA concentration are further examined herein. At a 1:1 formulation ratio all of the test variables tested demonstrated good stability. Size increases of 10–20 nm above the initial value were typical following incubation at 37° C. for 8 hours. Again, the complexes were more stable in the presence of albumin; this was more noticeable in the BODAI/cholesterol containing complexes than those formed with EDMPC/cholesterol. At a 3:1 ratio the BODAI/cholesterol containing complexes formed at the lowest DNA concentration precipitated, but the remaining complexes underwent very minor changes in size over the 8 hour incubation period and appeared to be relatively stable. The EDMPC containing complexes did not precipitate at this ratio. At the 3:1 ratio, there was very little difference between the aggregation induced by physiological salts or salts plus albumin.

2. DNA Concentration.

Complexes formed at 1:1 or 3:1 ratios did not show a stability response to salt or salt/albumin that correlated with DNA concentration. However, the 1:6 BODAI/cholesterol containing complexes demonstrated a clear association between DNA concentration and stability in physiological salts. At 0.3125 mglml, the complexes were relatively stable for 2 min 28s to 90 min, depending on the pH. As the DNA concentration was increased to 0.5 or 1.0 mg/ml, the stability dropped from 90 min to 1 min 52 s and from 2 min 28 s to 45s.

3. pH Effects.

BODAIcholesterol complexes formed at 3:1 or 1:6 DNA:lipid ratio with a concentration of 0.3125 mg/ml DNA, demonstrated reduced stability in physiological salt as the pH was increased from 5, to 6, to 7 (Table 2). This result was most pronounced in the BODAI/cholesterol containing complex formed at 0.3125 mg/ml. As the pH dropped, the stability time dropped from 90 min (pH 5), to 3:28 (pH 6) then 2:28 (pH 7).

Summary

Colloidal theory indicates that a dilute, homogeneous suspension is likely to be more stable than a concentrated, heterogeneous sample. Dilution of cationic lipid/DNA complexes can be achieved by direct addition of buffer to the complex, or by forming the complex at a low DNA concentration while maintaining the original DNA:lipid ratio. Precipitation occurred much faster in the complexes containing a high concentration of DNA than in those at low DNA concentrations. Aggregation in a colloidal suspension is dependent on a number of factors, including charge and pH. These factors influence the size/depth of the double layer surrounding each particle. As the double layer is reduced, the attractive van der Waals forces are able to overcome the weak repulsive forces between particles. In these experiments, a reduced pH correlated with extended stability in physiological salts. Inclusion of albumin in the physiological salt medium reduced the effects of the salts; thus, complexes were more stable in the presence of this protein. Notably, the 1:6 formulation complexes precipitated in the absence of a albumin but typically did not precipitate when albumin was present. Even after 8 hours, many of the complexes had undergone only minor changes in size.

Complexes formulated at pH 5 are more stable in physiological salts than those at pH 6 or 7. Complexes formulated at reduced DNA concentrations (0.3125 mg/ml) are more stable in physiological salt than those formed at high DNA concentrations (0.5 or 1.0 mg/ml). The inclusion of albumin in the physiological salt medium reduces complex instability. BODAI/cholesterol complexes are more stable when formulated at 1:1 and 3:1 ratios than EDMPC/cholesterol containing complexes formed at similar ratios.

Example 3

IP Delivery Screening for Expression in the SKOV-3 Tumor Model

Distribution and physical characterization analysis of lipid:DNA formulations delivered i.p. into nude mice revealed a number of limiting factors for successful transfection. Key issues included the rapid precipitation of complexes formulated at high lipid ratios, rapid degradation of unprotected DNA and inadequate distribution. To overcome these difficulties, complexes were formulated at a 1:6 or 1:8 (DNA:cationic lipid) ratio (to protect the DNA), then, in some cases, administered at one-third their original concentration (to increase distribution through reduced aggregation), either by direct dilution or formulation at the reduced concentration. EDMPC formulations were used as there was some indication that this lipid was preferentially taken up by the lymphatic system compared to other cationic lipid formulations. This is advantageous, as, following metastasis, the lymph nodes are a common site of tumor uptake. Thus, EDMPC-containing formulations can be transported via the lymph system into tumors. Multiple injection sites and administration methods were also tested.

Materials and Methods

1. Complexes.

In all cases, cationic lipid-DNA complexes were formulated with the Hamilton dilutor, using standard practice. Diluted formulations were formed in one of two ways, depending on the protocol. In one method, dilutions were performed by mixing the complexes at standard concentrations (e.g., DNA at 0.3 mg/ml) and then diluting the concentrated formulation in buffered 5% dextrose (weight/volume) (D5W) (e.g., to provide a 1/3 concentrate solution, e.g., 0.1 mg/ml). In another method, the complexes were initially formulated with the dilutor at the reduced concentration. The complexes were prepared using plasmid DNA encoding the CAT gene under the control of the CMV promoter.

2. Animal Studies.

2 ml of sample was injected intraperitoneally into SKOV-3 tumor nude mice. The original SKOV-3 cells were obtained from ATCC; however animals used for these experiments were injected with SKOV-3 tumor cells derived from various in vivo protocols. At 24 hr. the animals were harvested using $CO_2$; the peritoneal cavity was exposed and individual tumors harvested. The lungs, peritoneal sac and mesentery were also removed depending on the protocol requirements. Tissues were immediately frozen at $-80°$ C. and stored until analysis of CAT expression by ELISA.

Results

The main issues examined were complex precipitation, DNA protection and transfection efficiency, (e.g., transfection of tumors). For some formulations, lipid ratios of about 1:6–1:8 provided good DNA protection. Factors which reduced precipitation included: administration of multiple doses of diluted complex, reducing the concentration of lipid, improving the stability of the formulation, e.g., by reducing the pH to 5.0, reducing the DNA concentration (0.25 mg/ml provided good stability), and picking a more stable lipid formulation, e.g., EDMPC/DiPPE (1:1 molar ratio). For more stable formulations, dilution was not necessary. High levels of expression were observed and the number of transfected tumors with stable formulations was very high.

2. Expression Data/Free DNA Control.

Expression data from six protocols have been compiled and can be found in Table 3. A naked plasmid DNA control (4 mg total dose) was included in some of the protocols and produced CAT expression levels in tumors of 17.53+/−14.35 (4 of 8 animals expressed), 6.49+/−4.14 (2/7 animals expressed) and 23.30+/−18.08 pg/mg (3/7 animals expressed) total protein CAT, respectively. A similar dose achieved expression of 7.86+/−6.43 (4/10 tumors expressed) and 8.99+/−5.31 (4/21 tumors expressed) in other protocols. When naked DNA control concentration was reduced to 1 mg/ml total dose, no activity was observed.

TABLE 3

| Expression - animal # | | Expression (pg/mg) | | | |
|---|---|---|---|---|---|
| Tumor | Lung | Tumor | Lung | Formulation | |
| 0 | 1/8 | | 4.93 | DNA | 0.5 mg/ml |
| 1/8 | 3/9 | 12.5 | 49.91 | 1:6-EDMPC/Chol | 0.3 mg/ml |
| 0 | 0 | | | 1:1-EDMPC/Chol | 2.0 mg/ml |
| 0 | 0 | | | 3:1-EDMPC/Chol | 0.6 mg/ml |
| 0 | 0 | | | DNA | 2.0 mg/ml |
| 4/7 | 0 | 18.83 ± 3.83 | | 1:6-BODAI/Chol | 0.3 mg/ml |
| 0 | 0 | | | 3:1-EDMPC/Chol | 0.6 mg/ml |
| 3/7 | — | 23.20 ± 18.08 | | DNA | 2.0 mg/ml |
| 1/6 | — | 15.91 | | 3:1-EDMPC/Chol | 0.6 mg/ml |
| 5/5 | — | 20.61 ± 8.14 | | 3:1-EDMPC/Chol | injected at several sites |
| 5/6 | — | 57.23 ± 32.45 | | 1:6-EDMPC/Chol | 0.3 mg/ml |
| 6/8 | — | 69.25 ± 60.95 | | 1:6-EDMPC/Chol | dil. to 0.1 mg/ml, 3 doses |
| 6/7 | — | 67.62 ± 61.81 | | 1:6-EDMPC/Chol | formed at 0.1 mg/ml doses |
| 4/10 | — | 7.86 ± 6.43 | | DNA | 2.0 mg/ml |
| 8/15 | — | 34.67 ± 38.58 | | 1:6 EDMPC/Chol | 0.3 mg/ml |
| 9/11 | — | 88.21 ± 116.44 | | 1:6-EDMPC/Chol | dil. to 0.1 mg/ml, 3 doses |
| 7/23 | — | 108.09 ± 196.32 | | 1:6-EDMPC/Chol | dil. to 0.1 mg/ml, 1 dose |
| 16/19 | — | 93.22 ± 108.61 | | 1:6-EDMPC/ DOPE | 0.3 mg/ml |
| 13/18 | — | 213.36 ± 181.46 | | 1:6-EDMPC/ DOPE | dil. to 0.1 mg/ml, 3 doses |
| 20/20 | — | 390.87 ± 478.00 | | 1:8-EDMPC/ DiPPE | 0.25 mg/ml |
| 13/15 | — | 410.00 ± 651.16 | | 1:8-EDMPC/ DiPPE | dil. to 83 ug/m, 3 doses |
| 4/21 | — | 8.99 ± 5.31 | | DNA | 2.0 mg/ml |
| 16/18 | — | 212.54 ± 270.11 | | 1:6-EDMPC/ DOPE | 0.3 mg/ml |
| 22/23 | — | 349.4 ± 620.47 | | 1:8-EDMPC/ DiPPE | 0.25 mg/ml |

3. Lipid:DNA Complexes.

As shown in Table 3, CAT expression within tumors was achieved with the following formulations: 3:1 DNA:EDMPC/Chol (DNA at 0.6 mg/ml); 1:6 BODAI/Chol (DNA at 0.3 mg/ml); 1:6 DNA:EDMPC/Chol (DNA at 0.3 mg/ml); a dilution of 1:6 DNA:EDMPC/Chol (DNA at 0.3 mg/ml) to a DNA concentration of 0.1 mg/ml (dilutions administered in three doses); 1:6 DNA:EDMPC/DOPE (DNA at 0.3 mg/ml); 1:8 EDMPC/DiPPE (DNA at .0.25 mg/ml).

m3:1 DNA:EDMPC/Chol (DNA at 0.6 mg/ml) and 1:6 BODAI/Chol (DNA at 0.3 mg/ml) produced low levels of expression (maximum 20.61 pg/mg, total protein) 20 in a limited number of animals per test variable. By comparison 1:6 DNA:EDMPC/Chol (DNA at 0.3 mg/ml) resulted in three-fold greater CAT expression than either 3:1 DNA:EDMPC/Chol (DNA at 0.6 mg/ml) or 1:6 BODAI/Chol (DNA at 0.3 mg/ml). In addition, 1:6 DNA:EDMPC/Chol (DNA at 0.3 mg/ml) resulted in about 75% of the animals demonstrating CAT expression within peritoneal tumors. By modifying the helper lipid type and DNA to lipid ratio, these values were increased to 212.54+/−270.11 and 93.22+/−108.61 (1:6 DNA:EDMPC/DOPE (DNA at 0.3 mg/ml)) and 390.87+/−478 and 349.4+/−620.47 (1:8 EDMPC/DiPPE (DNA at 0.25 mg/ml). Formulations of 1:8 EDMPC/DiPPE (DNA at 0.25 mg/ml) were tested in vivo by i.p. adrninistration into the SKOV-3 murine model following formulation at three different pH values, pH 5, 6, and 7. Similar in vivo expression of the CAT marker gene was achieved for each formulation.

4. Modification of the Delivery Methodology.

Multiple injection of 3:1 DNA:EDMPC/Chol (DNA at 0.6 mg/ml) over several sites produced the same level of CAT expression as injection at a single site (16–21 pg/mg total protein), yet all of the tumors tested (5/5) demonstrated CAT production, as compared to 1/6 tumors for the single dose test group. 1:6 DNA:EDMPC/Chol (DNA at 0.3 mg/ml), either at the original concentration or in the diluted form (DNA at 0.1 mg/ml) transfected tumors in the majority of the animals tested (5/6, 6/8, 6/7), at a similar mean CAT level of expression (57, 69 and 67 pg/mg total protein). Formulations 1:6 DNA:EDMPC/DOPE (DNA at 0.3 mg/ml) and 1:8 EDMPC/DiPPE (DNA at 0.25 mg/ml) were also administered as single, 2 ml doses, or 3×2 ml doses of 3×diluted formulations (i.e., same fmal dose of DNA in 3 times the volume). 1:6 DNA:EDMPC/DOPE (DNA at 0.3 mg/ml) and 1:8 EDMPC/DiPPE (DNA at 0.25 mg/ml) achieved CAT expression values in both diluted and non-diluted forms (93 and 213 pg/mg total protein with DOPE as the helper lipid and 390 and 410 pg/mg total protein with DiPPE as the helper lipid).

TABLE 4

| Protocol | Composition | | Comments |
|---|---|---|---|
| Active | | | |
| Multi-site | 1:6-BODAI/Chol | 0.3 mg/ml | 18.83 ± 3.83 pg/mg protein |
| One dose | 1:6-EDMPC/Chol | 0.3 mg/ml | 57.23 ± 32.45 pg/mg protein |
| 3 dil. doses | 1:6-EDMPC/Chol | 0.1 mg/ml | 69.25 ± 60.95 pg/mg protein |
| 3 dil. doses | 1:6-EDMPC/Chol | 0.1 mg/ml | 67.62 ± 61.82 pg/mg protein |
| One dose | 1:6-EDMPC/DOPE | 0.3 mg/ml | 93.22 ± 108.61 pg/mg protein |
| 3 dil. doses | 1:6-EDMPC/DOPE | 0.1 mg/ml | 213.36 ± 181.46 pg/mg protein |
| One dose | 1:8-EDMPC/DiPPE | 0.25 mg/ml | 390.87 ± 478.00 pg/mg protein |
| 3 dil. doses | 1:8-EDMPC/DiPPE | 0.083 mg/ml | 410.00 ± 651.16 pg/mg protein |
| Inactive | | | |
| | 1:1-EDMPC/Chol | 2.0 mg/ml | Chol = cholesterol |
| | 3:1-EDMPC/Chol | 0.6 mg/ml | |
| | 1:6.5-EDMPC/Chol | 0.3 mg/ml | |

TABLE 5

Activity (pg/mg total protein) & number of animals/tumors showing expression

| Formulation | Peritoneal Sac injection site | | contralateral side | | Mesentery | | Tumor Expression | | A = animals T = tumors |
|---|---|---|---|---|---|---|---|---|---|
| D5W | 0 | 0/2 | 0 | 0/2 | 0 | 0/2 | 0 | | 0/2 A |
| DNA | 12.74 ± 8.59 | 4/7 | 27.29 ± 27.68 | 5/6 | 35.80 ± 20.97 | 3/5 | 23.20 ± 18.08 | | 3/5 A |
| 3:1-EDMPC/Chol - one dose | 4.57 ± 0.83 | 3/7 | 13.51 ± 4.05 | 4/7 | 72.05 | 1/5 | 15.91 | | 1/6 A |
| 3:1-EDMPC/Chol - multi site | 41.16 ± 37.09 | 7/7 | 28.92 ± 40.08 | 6/7 | 10.38 | 1/6 | 20.61 ± 8.14 | | 5/5 A |
| 1:6-EDMPC/Chol - one dose | 39.84 ± 24.60 | 6/7 | 15.75 ± 12.18 | 6/7 | 81.81 ± 99.13 | 6/7 | 57.23 ± 32.45 | | 5/6 A |
| 1:6-EDMPC/Chol - 3 dil doses | 183.90 ± 170.58 | 6/8 | 130.52 ± 122.08 | 6/8 | 362.28 ± 475.22 | 6/7 | 69.25 ± 60.95 | | 6/8 A |
| 1:6-EDMPC/Chol - 3 dil doses | 114.99 ± 199.84 | 8/8 | 162.45 ± 344.92 | 8/8 | 193.56 ± 246.68 | 5/5 | 67.62 ± 61.82 | | 6/7 A |
| 1:6-EDMPC/DOPE - one dose | — | | — | | — | | 93.22 ± 108.61 | | 16/19 T |
| 1:6-EDMPC/DOPE - 3 dil doses | — | | — | | — | | 213.36 ± 181.46 | | 13/18 T |
| 1:8-EDMPC/DiPPE - one dose | — | | — | | — | | 390.87 ± 478.00 | | 20/20 T |
| 1:8-EDMPC/DiPPE - 3 dil doses | — | | — | | — | | 410.00 ± 651.16 | | 13/15 T |

Lipid/DNA complex screening combined with in vivo deliverylcharacterization data revealed that DNA protection and complex precipitation are problems that are overcome to enable optimal DNA delivery and transfection within peritoneal tumors. Complexes formulated at a 1:6 or 1:8 ratio (good DNA protection) demonstrate higher transfection activities than those formulated at lower lipid concentrations. Dilution of the complex to reduce precipitation did not make a great difference to the average transfection activity in tumors, especially in those formulations resulting in high levels of expression (e.g., 1:6 DNA:EDMPC/DOPE (DNA at 0.3 mg/ml) and 1:8 EDMPC/DiPPE (DNA at 0.25 mg/ml) and various dilutions thereof). EDMPC/cholesterol formulated in the 1:6 ratio is more effective than BODAI/cholesterol. There is some evidence that EDMPC/cholesterol containing complexes were taken up by the lymphatic system more readily than BODAI/cholesterol containing formulations. Delivery of the complex at multiple (different) injection sites appeared to overcome the restricted distribution of the formulation observed in the animal distribution studies. As greater than 90% distribution of 1:8 EDMPC/DiPPE (DNA at 0.25 mg/ml) (55/58 tumors expressed CAT) following single administration, multiple injections were unnecessary for this formulation.

In summary, when complex precipitation is minimized to ensure good distribution and long half-life of the formulation, transfection is improved. DNA protection is maintained to ensure that an "active" plasmid is delivered to the target tissue. Dilution of the complex does not reduce tumor derived CAT expression compared to the concentrated formulation, when delivering similar final concentrations of DNA and lipid. Naked DNA showed low transffection efficiency when delivered alone. Finally, 1:8 EDMPC/DiPPE (DNA at 0.25 mg/ml) was an extremely effective formulation.

Example 4

Intra-peritoneal Formulation for Tumor Delivery—Neutral Lipid Comparisons

Complexes tested were 1) Naked DNA at 2 mg/ml; 2) DNA:EDMPC/Cholesterol; 3) DNA:EDMPC/DOPE, and 4) DNA:EDMPC/DiPPE. Complexes were formulated at a 1:6 ratio DNA:cationic lipid in 2.5 mM Histidine pH 5.0, 5% w/v dextrose. All animal experiments were carried out as 2 ml i.p. injections into SKOV-3 tumored nude mice. Tumors were harvested at 24 hr. EDMPC/DiPPE was also administered to A2780 and PA1 tumor bearing mice, both of which had ascites. The SKOV-3 model used in the examples above have solid tumors only,. without ascites.

In examination of tumors isolated from the mice, the following results were observed: 1) DNA:EDMPC/DiPPE, DNA:EDMPC/DOPE, and DNA:EDMPC/Cholesterol resulted in tumor uptake and expression greater than naked DNA in the animals. DNA:EDMPC/DiPPE was more effective than DNA:EDMPC/DOPE, which was more effective than DNA:EDMPC/Cholesterol, which was more effective than naked DNA. All of the tumors transfected with DNA:EDMPC/DiPPE expressed CAT and gave consistent levels of CAT tumor expression up to 3 days post-administration. There was a refractory period.

In an in vitro experiment using SKOV-3 cells obtained from tumored animals, again, DNA:EDMPC/DiPPE was more effective than DNA:EDMPC/DOPE, which was more effective than DNA:EDMPC/Cholesterol, which was more effective than Naked DNA.

The above examples showed that EDMPC containing complexes had greater stability in peritoneal fluid than other cationic lipids. The neutral lipid component and pH of the complexes was varied to optimize complex stability. EDMPC/DiPPE had the greatest stability in a physiological salt environment of the formulations tested. For all formulations tested, relative stability in salt correlates with in vivo expression levels following i.p. administration.

In an additional aspect, the present invention provides kits embodying the methods, compositions and apparatus herein. Kits of the invention optionally comprise one or more of the following: (1) a composition, apparatus or apparatus component as described herein; (2) instructions for practicing the methods described herein, and/or for operating the apparatus or apparatus components or using the compositions herein; (3) one or more assay component; (4) a container for holding compositions, apparatus or assay components, and, (5) packaging materials.

In a further aspect, the present invention provides for the use of any composition, apparatus, apparatus component or kit herein, for the practice of any method or assay herein, and/or for the use of any composition, apparatus or kit to practice any assay or method herein.

Accordingly, the disclosures and descriptions herein are intended to be illustrative, but not limiting, of the scope of the invention which is set forth in the following claims. All patents and publications cited herein are incorporated in their entirety for all purposes, as though each were individually indicated to be incorporated by reference.

What is claimed is:

1. A method of transfecting a cell within a peritoneal cavity of a mammal, the method comprising; administering a nucleic acid:lipid complex to the peritoneal cavity of the mammal, the complex comprising a nucleic acid, O-ethyl-dimyristoylphosphatidylcholine (EDMPC), and a neutral lipid, wherein the ratio of selected nucleic acid to EDMPC is between about 1:3 to about 1:20 μg nucleic acid:nmole EDMPC.

2. The method of claim 1, wherein the neutral lipid is 1,2 diphytanoyl-sn-glycero-3-phosphoethanolamine (DiPPE) or dioleoylphosphatidylethanolamine (DOPE).

3. The method of claim 1, wherein the neutral lipid is DiPPE.

4. The method of claim 1, wherein the cell is a tumor cell.

5. The method of claim 1, further comprising multiple administration of the nucleic acid:lipid complex.

6. The method of claim 1, wherein the nucleic acid is DNA.

7. The method of claim 6, wherein the DNA encodes a protein.

8. The method of claim 1, wherein the nucleic acid is present at a concentration ranging from about 0.1 to 1.0 mg/ml.

9. The method of claim 1, wherein the ratio of selected nucleic acid to EDMPC in the composition is about 1:8 μg nucleic acid:nmole EDMPC.

10. The method of claim 9, wherein the neutral lipid is DiPPE and in which EDMPC and DiPPE are in a 1:1 molar ratio.

11. The method of claim 10, wherein the DNA is present at a concentration of about 0.25 mg/ml.

12. The method of claim 11, wherein the complex is in a composition comprising a 2.5 mM histidine buffer at pH 5.0 and 5% w/v dextrose.

13. The method of claim 1, wherein the complex further comprises a target-specific moiety.

14. The method of claim 13, wherein the target-specific moiety comprises a ligand or a receptor which binds a molecule of interest.

15. The method of claim 14, wherein the ligand selectively binds to cancer cells.

16. A composition comprising a nucleic acid:lipid complex comprising EDMPC, DiPPE and a nucleic acid, wherein the ratio of selected nucleic acid to EDMPC is between about 1:3 to about 1:20 μg nucleic acid:nmole EDMPC.

17. The composition of claim 16, wherein the nucleic acid is DNA.

18. The composition of claim 17, wherein the DNA encodes a protein.

19. The composition of claim 16, wherein the nucleic acid is present at a concentration ranging from about 0.1 to 1.0 mg/ml.

20. The composition of claim 16, wherein the ratio of selected nucleic acid to EDMPC in the composition is about 1:8 μg nucleic acid:nmole EDMPC.

21. The composition of claim 20, wherein the neutral lipid is DiPPE and in which EDMPC and DIPPE are in a 1:1 molar ratio.

22. The composition of claim 21, wherein the DNA is present at a concentration of about 0.25 mg /ml.

23. The composition of claim 22, wherein the complex is in a composition comprising a 2.5 mM histidine buffer at pH 5.0 and 5% w/v dextrose.

24. The composition of claim 16, wherein the complex comprises a target-specific moiety.

25. The composition of claim 24, wherein the target-specific moiety comprises a ligand or a receptor which binds a molecule of interest.

26. The composition of claim 25, wherein the ligand selectively binds to cancer cells.

* * * * *